US010751394B2

(12) United States Patent
Johnson et al.

(10) Patent No.: US 10,751,394 B2
(45) Date of Patent: Aug. 25, 2020

(54) NEUROTOXINS AND USES THEREOF

(71) Applicant: CELLSNAP LLC, Madison, WI (US)

(72) Inventors: Eric A. Johnson, Madison, WI (US); Sabine Pellett, Madison, WI (US); William H. Tepp, Madison, WI (US); Christina Pier, Madison, WI (US); Marite Bradshaw, Madison, WI (US)

(73) Assignee: CELLSNAP LLC, Madison, WI (US)

( * ) Notice: Subject to any disclaimer, the term of this patent is extended or adjusted under 35 U.S.C. 154(b) by 0 days.

(21) Appl. No.: 15/793,628

(22) Filed: Oct. 25, 2017

(65) Prior Publication Data

US 2018/0117129 A1 May 3, 2018

Related U.S. Application Data

(60) Provisional application No. 62/412,456, filed on Oct. 25, 2016.

(51) Int. Cl.
*A61K 38/48* (2006.01)
*A61P 25/00* (2006.01)

(52) U.S. Cl.
CPC .......... *A61K 38/4893* (2013.01); *A61P 25/00* (2018.01); *Y02A 50/469* (2018.01); *Y02A 50/473* (2018.01)

(58) Field of Classification Search
None
See application file for complete search history.

(56) References Cited

U.S. PATENT DOCUMENTS

| 5,939,070 | A | * | 8/1999 | Johnson | ............... | C07K 14/33 |
| | | | | | | 424/194.1 |
| 6,444,209 | B1 | * | 9/2002 | Johnson | ............... | C07K 14/33 |
| | | | | | | 424/194.1 |
| 8,440,204 | B2 | * | 5/2013 | Johnson | ............... | A61K 39/08 |
| | | | | | | 424/239.1 |
| 8,940,477 | B2 | * | 1/2015 | Johnson | ............... | C12Q 1/37 |
| | | | | | | 435/4 |
| 9,217,172 | B2 | * | 12/2015 | Johnson | ............ | G01N 33/5073 |
| 9,453,057 | B2 | * | 9/2016 | Johnson | ............... | C07K 14/33 |
| 10,253,074 | B2 | * | 4/2019 | Johnson | ............... | C12N 15/09 |
| 2012/0164657 | A1 | * | 6/2012 | Johnson | ............... | C12Q 1/37 |
| | | | | | | 435/7.1 |
| 2014/0170133 | A1 | | 6/2014 | Frevert | | |
| 2014/0234857 | A1 | * | 8/2014 | Johnson | ............ | G01N 33/5073 |
| | | | | | | 435/7.1 |
| 2018/0117129 | A1 | * | 5/2018 | Johnson | ............ | A61K 38/4893 |
| 2018/0193435 | A1 | * | 7/2018 | Johnson | ........... | C12Y 304/2406 |

FOREIGN PATENT DOCUMENTS

| EP | 3312290 A1 * | 4/2018 | ............... C12Q 1/37 |
| WO | WO 2016/156113 | 10/2016 | |
| WO | WO-2017091315 A1 * | 6/2017 | ........ H04W 72/0453 |
| WO | WO-2018073370 A1 * | 4/2018 | ............ C07K 14/47 |
| WO | WO-2018081282 A1 * | 5/2018 | .............. A61P 25/00 |
| WO | WO-2018132423 A1 * | 7/2018 | ..... C12Y 304/24069 |

OTHER PUBLICATIONS

Barash et al, Journal Infectious Diseases, 2014, 209:183-191. electronically published Oct. 7, 2013 (Year: 2014).*
Dover et al, Journal Infectious Diseases, 2014, 209:192-202. electronically published Oct. 7, 2013 (Year: 2014).*
Fan et al, Journal Infectious Diseases, 2016, 213:1606-1614. electronically published Mar. 1, 2016 (Year: 2016).*
Kalb et al, Anal. Chem., Apr. 7, 2015. 87/7:3911-3917. (Year: 2015).*
Maslanka et al, Journal Infectious Diseases, 2015, 213:379-385. electronically published Jun. 10, 2015 (Year: 2015).*
Pellett et al, Toxicon, 2018, 147:38e46. available online Dec. 19, 2017 (Year: 2017).*
Pellett et al, Abstracts/Toxicon 93, 2015, p. S48, Abstract#156 (Year: 2015).*
Raphael et al, Applied and Environmental Microbiology, Jul. 2010. 76/14:4805-4812. published ahead of print: May 28, 2010 (Year: 2010).*
Chaddock, J. et al. "Engineering toxins for 21st century therapies", FEBS J., Apr. 2011 (Apr. 2011), vol. 278, No. 6, pp. 899-904.
Dressler, D., "Botulinum toxin drugs: Brief history and outlook", J Neural Transm (Vienna), Mar. 2016 (Mar. 2016), vol. 123, No. 3, pp. 277-279.
Dressler, D. "Clinical applications of botulinum toxin", Curr opin microbiol, Jun. 2012 (Jun. 2012); vol. 15, No. 3, pp. 325-336.
Dressler, D. "Pharmacology of botulinum toxin drugs", HNO, Jun. 7, 2012 (Jun. 7, 2012), vol. 60, No. 6, pp. 496-502. English Abstract Provided.
Fischer, A, et al. "Bimodal modulation of the botulinum neurotoxin protein-conducting channel", Proc Natl Acad Sci USA, Feb. 3, 2009 (Feb. 3, 2009), vol. 106, No. 5, pp. 1330-1335.
Fischer, A. et al. "Crucial Role of the Disulfide Bridge between Botulinum Neurotoxin Light and Heavy Chains in Protease Translocation across Membranes", J Biol Chem, May 1, 2007 (May 1, 2007), vol. 282, No. 40, pp. 29604-29611.
Fischer, A. et al. "Single molecule detection of intermediates during botulinum neurotoxin translocation across membranes", Proc Natl Acad Sci USA, Jun. 19, 2007 (Jun. 19, 2007), vol. 104, No. 25, pp. 10447-10452.
Gimenez, D., et al. "The Typing of Botulinal Neurotoxins", Int J Food Microbiol Sep. 1995 (Sep. 1995), vol. 27, No. 1, pp. 1-9.
Montecucco, C., et al. "Mechanism of action of tetanus and botulinum neurotoxins", Mol Microbiol, Jul. 1994 (Jul. 1994), vol. 13, No. 1, pp. 1-8.

(Continued)

*Primary Examiner* — Nita M. Minnifield
(74) *Attorney, Agent, or Firm* — Casimir Jones, S.C.

(57) ABSTRACT

The present disclosure relates to neurotoxins and uses thereof. In particular, provided herein are botulinum neurotoxins with altered properties and uses thereof (e.g., research, screening, and therapeutic uses).

7 Claims, 3 Drawing Sheets

Specification includes a Sequence Listing.

(56) References Cited

OTHER PUBLICATIONS

Montecucco, C. et al., "Presynaptic receptor arrays for clostridial neurotoxins", Oct. 2004 (Oct. 2004), Trends in Microbiology, vol. 12, No. 10, pp. 442-446.
Pirazzini, M., et al., "Thioredoxin and Its Reductase are Present on Synaptic Vesicles, and Their Inhibition Prevents the Paralysis Induced by Botulinum Neurotoxins", Cell Rep., Sep. 25, 2014 (Sep. 25, 2014), vol. 8, No. 6, pp. 1870-1878.
Wortzman, M. et al., "The Science and Manufacturing Behind Botulinum Neurotoxin Type A-ABO in Clinical Use", Surg J., Nov. 2009 (Nov. 2009), vol. 29, No. 65, pp. S34-S42.
International Search Report, International Patent Application No. PCT/US2017/058308, dated Feb. 9, 2018.
Pellett et al. Purification and Characterization of Botulinum Neurotoxin FA from a Genetically Modified Clostridium botulinum Strain. mSphere Feb. 2016, vol. 1(1), p. 1-18.
Yao et al. Crystal Structure of the Receptor-Binding Domain of Butulinum Neurotoxin Type HA, Also Known as Type FA or H. Toxins (Basel) Mar. 2017, vol. 9(3), p. 1-13.

* cited by examiner

FIG. 2 Continued
C

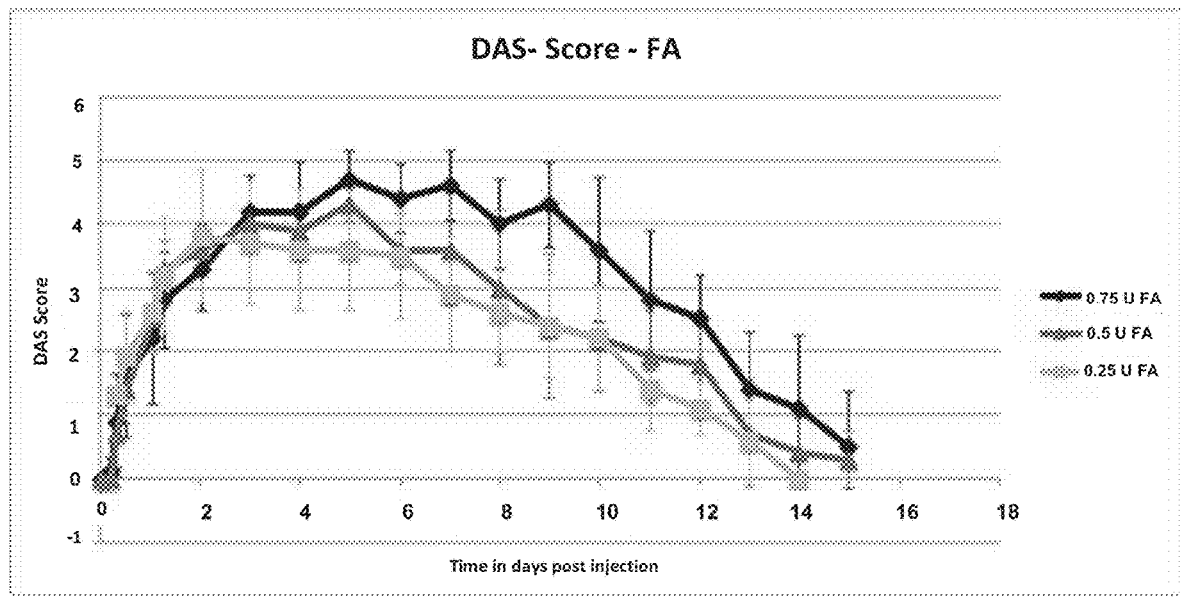

FIG. 3

```
   1 mpvvinsfny ddpvndntii yirppyyets ntyfkafqim dnvwiipery rlgidpslfn
  61 ppvslkagsd gyfdpnylst nteknkylqi miklfkrins kpaqqillee iknaipylgn
 121 sytqeeqftt nnrtvsfnvk langnivqqm anliiwgpgp dlttnktqgi iyspyqsmea
 181 tpykdgfgsi mtvefspeya tafndisias hspslfikdp alilmhelih vlhglygtyi
 241 teykitpnvv qsymkvtkpi tsaefltfgg rdrnivpqsi qsqlynkvls dykriasrln
 301 kvntatalin idefknlyew kyqfakdsng vysvdlnkfe qlykkiysft efnlayefki
 361 ktrlgylaen fgpfylpnll ddsiytevdg fnigalsiny qgqnigsdin sikklqgqgv
 421 vsrvvrlcsn sntknslcit vnnrdlffia sqesygenti ntykeiddtt tldpsfedil
 481 dkvilnfneq vipqmpnrnv stdiqkdnyi pkydynrtdi idsyevgrny ntffylnaqk
 541 fspnesnitl tssfdtglle gskvytffss dfinninkpv qallfiewvk qvirdfttea
 601 tktstvdklk dislvvpyig lalnigdeiy kqhfaeavel vgaglllefs pefliptili
 661 ftikgyltgs irdkdkiikt ldnalnvrdq kwkelyrwvv skwlttintq fnkrkeqmyk
 721 alknqataik kiienkynny ttdekskids synineiert lnekinlamk nieqfitess
 781 iayliniinn etiqklksyd dlvrryllgy irnhssilgn sveelnskvn nhldngipfe
 841 lssytndsll iryfnknyge lkyncilnik yemdrdklvd ssgyrsrini gtgvkfseid
 901 knqvqlsnle sskievilnn gviynsmyen fstsfwirip kyfrninney kiiscmqnns
 961 qwevslnfsn mnskiiwtlq dtegikktvv fqytqninis dyinrwifvt itnnrlsnsk
1021 iyingrline esisdlgnih asnnimfkld gcrdphryiw ikyfnlfdke lnkkeikdly
1081 dnqsnsqilk dfwgdylqyd kpyymlnlyd pnkyldvnnv girgymylkg prgrivttni
1141 ylnstlymgt kfiikkyasg nkdnivrnnd rvyinvvvkn keyrlatnas qagvekilsa
1201 veipdvgnls qvvvmksend qgirnkckmn lqdnngndig figfhqfnni aklvasnwyn
1261 rqigkasrtf gcswefipvd dgwgessl
```

(SEQ. ID NO: 1)

NEUROTOXINS AND USES THEREOF

CROSS-REFERENCE TO RELATED APPLICATIONS

This application claims the benefit of U.S. provisional application Ser. No. 62/412,456, filed Oct. 25, 2016, which is incorporated herein by reference in its entirety.

STATEMENT REGARDING FEDERALLY SPONSORED RESEARCH OR DEVELOPMENT

This invention was made with government support under grant number RO1A095274 awarded by National Institute of Allergy and Infectious Diseases. The government has certain rights in the invention.

FIELD OF THE DISCLOSURE

The present disclosure relates to neurotoxins and uses thereof. In particular, provided herein are botulinum neurotoxins with altered properties and uses thereof (e.g., research, screening, and therapeutic uses).

BACKGROUND OF THE DISCLOSURE

Botulinum neurotoxins (BoNTs), synthesized by the Gram-positive, soil-dwelling bacterium *Clostridium botulinum*, are the most toxic substances known to humankind and are the causative agents of the neuroparalytic disease botulism (Johnson E (2005) in *Topley and Wilson's microbiology and microbial infections*, ed S. P. Borriello, P. R. Murray, and G. Funke (Hodder Arnold, London, United Kingdom), pp 1035-1088). Seven immunologically distinct serotypes of BoNTs designated A through G have been described (Gimenez D F & Gimenez J A (1995) *Int Food Microbiol* 27: 1-9). BoNTs are initially synthesized as a single-chain polypeptide of ~150 kDa, but posttranslational proteolytic cleavage yields distinct heavy and light chains (HC and LC) of ~100 kDa and ~50 kDa linked by a disulfide bond. The HC is further functionally divided into the $HC_C$ and $HC_N$ subdomains. The $HC_C$ domain is responsible for recognition and binding to specific neuronal cell surface receptors leading to endocytosis, while the $HC_N$ domain is responsible for channel formation in the endocytic vesicle membrane and translocation and internalization of the LC across the endosomal membrane (Montecucco et al., (2004) *Trends Microbiol* 12: 442-446; Fischer A & Montal M (2007) *J Biol Chem* 282: 29604-29611; Fischer A, et al (2009) *Proc Natl Acad Sci USA* 106: 1330-1335). After translocation, the disulfide bond is cleaved, and the LC is released into the cell cytosol and refolded to the active enzyme component as a zinc-dependent endopeptidase (Fischer et al., supra; Fischer A & Montal M (2007) *Proc Natl Acad Sci USA* 104: 10447-10452; Pirazzini, et al., *Cell Rep* 2014, 8, 1870-1878). The LC then specifically targets and cleaves an intracellular SNARE protein at the pre-synaptic vesicles, which leads to inhibition of neurotransmitter release. Each BoNT serotype has a distinct cleavage target, with BoNT/A and E cleaving SNAP-25 at distinct sites, BoNT/B, D, F, and G cleaving VAMP/synaptobrevin at different sites, and BoNT/C cleaving both SNAP-25 and syntaxin (reviewed in Montecucco C & Schiavo G (1994) *Mol Microbiol* 13: 1-8).

BoNT/A and to a much lesser extent BoNT/B are used as unique and important pharmaceuticals to treat a variety of neuromuscular disorders and in cosmetics. Conditions for which the Food and Drug Administration approved the use of BoNTs include cosmetic treatments and to temporarily relieve a variety of muscle spasticity disorders, hyperhydrosis and migraines (Chaddock J A & Acharya K R (2011) *FEBS J* 278: 899-904). Cosmetic and clinical applications of BoNTs are increasing, and new formulations of BoNTs for pharmaceutical purposes are being developed necessitating clinical trials, accurate potency determination, and neutralizing antibody screening. For example, BoNTs are pharmaceutically administered for the treatment of pain disorders, voluntary muscle strength, focal dystonia, including cervical, cranial dystonia, and benign essential blepharospasm, hemifacial spasm, and focal spasticity, gastrointestinal disorders, hyperhidrosis, and cosmetic wrinkle correction, Blepharospasm, oromandibular dystonia, jaw opening type, jaw closing type, bruxism, Meige syndrome, lingual dystonia, apraxia of eyelid, opening cervical dystonia, antecollis, retrocollis, laterocollis, torticollis, pharyngeal dystonia, laryngeal dystonia, spasmodic dysphonia/adductor type, spasmodic dysphonia/abductor type, spasmodic dyspnea, limb dystonia, arm dystonia, task specific dystonia, writer's cramp, musician's cramps, golfer's cramp, leg dystonia, thigh adduction, thigh abduction knee flexion, knee extension, ankle flexion, ankle extension, equinovarus, deformity foot dystonia, striatal toe, toe flexion, toe extension, axial dystonia, pisa syndrome, belly dancer dystonia, segmental dystonia, hemidystonia, generalised dystonia, dystonia in lubag, dystonia in corticobasal degeneration, dystonia in lubag, tardive dystonia, dystonia in spinocerebellar ataxia, dystonia in Parkinson's disease, dystonia in Huntington's disease, dystonia in Hallervorden-Spatz disease, dopa-induced dyskinesias/dopa-induced dystonia, tardive dyskinesias/tardive dystonia, paroxysmal dyskinesias/dystonias, kinesiogenic non-kinesiogenic action-induced palatal myoclonus, myoclonus myokymia, rigidity, benign muscle cramps, hereditary chin trembling, paradoxic jaw muscle activity, hemimasticatory spasms, hypertrophic branchial myopathy, maseteric hypertrophy, tibialis anterior hypertrophy, nystagmus, oscillopsia supranuclear gaze palsy, epilepsia, partialis continua, planning of spasmodic torticollis operation, abductor vocal cord paralysis, recalcitrant mutational dysphonia, upper oesophageal sphincter dysfunction, vocal fold granuloma, stuttering Gilles de la Tourette syndrome, middle ear myoclonus, protective larynx closure, postlaryngectomy, speech failure, protective ptosis, entropion sphincter Odii dysfunction, pseudoachalasia, nonachalsia, oesophageal motor disorders, vaginismus, postoperative immobilisation tremor, bladder dysfunction, detrusor sphincter dyssynergia, bladder sphincter spasm, hemifacial spasm, reinnervation dyskinesias, cosmetic use craw's feet, frowning facial asymmetries, mentalis dimples, stiff person syndrome, tetanus prostate hyperplasia, adipositas, treatment infantile cerebral palsy strabismus, mixed paralytic concomitant, after retinal detachment surgery, after cataract surgery, in aphakia myositic strabismus, myopathic strabismus, dissociated vertical deviation, as an adjunct to strabismus surgery, esotropia, exotropia, achalasia, anal fissures, exocrine gland hyperactivity, Frey syndrome, Crocodile Tears syndrome, hyperhidrosis, axillar palmar plantar rhinorrhea, relative hypersalivation in stroke, in Parkinsosn's, in amyotrophic lateral sclerosis, spastic conditions, in encephalitis and myelitis autoimmune processes, multiple sclerosis, transverse myelitis, Devic syndrome, viral infections, bacterial infections, parasitic infections, fungal infections, in hereditary spastic paraparesis postapoplectic syndrome hemispheric infarction, brainstem infarction, myelon infarction, in central nervous system trauma, hemispheric lesions, brainstem lesions, myelon lesion, in central nervous system hemorrhage, intracerebral hemorrhage, subarachnoidal hemorrhage, subdural hemorrhage, intraspinal hemorrhage, in neoplasias, hemispheric tumors, brainstem tumors, and myelon tumor.

BoNT with optimized properties for the particular condition being treated or other usage are needed.

SUMMARY OF THE DISCLOSURE

The present disclosure relates to neurotoxins and uses thereof. In particular, provided herein are botulinum neurotoxins with altered properties and uses thereof (e.g., research, screening, and therapeutic uses).

Provided herein are BoNT/FA toxins and uses thereof (e.g., therapeutic uses). In some embodiments, the BoNT/FA is at least 90% (e.g., at least 90%, 91%, 92%, 93%, 94%, 95%, 96%, 97%, 98%, 99%, or 100%) identical to SEQ ID NO:1. In some embodiments, the heavy or light chain of the BoNT/FA is combined in a chimeric BoNT with a heavy or light chain from a different serotype of BoNT. Further embodiments provide nucleic acids and vectors encoding such amino acid sequences.

The BoNT/FA toxins described herein find use in a variety of therapeutic and cosmetic applications (e.g., pain disorders, voluntary muscle strength, focal dystonia, including cervical, cranial dystonia, and benign essential blepharospasm, hemifacial spasm, and focal spasticity, gastrointestinal disorders, hyperhidrosis, and cosmetic wrinkle correction, Blepharospasm, oromandibular dystonia, jaw opening type, jaw closing type, bruxism, Meige syndrome, lingual dystonia, apraxia of eyelid, opening cervical dystonia, antecollis, retrocollis, laterocollis, torticollis, pharyngeal dystonia, laryngeal dystonia, spasmodic dysphonia/adductor type, spasmodic dysphonia/abductor type, spasmodic dyspnea, limb dystonia, arm dystonia, task specific dystonia, writer's cramp, musician's cramps, golfer's cramp, leg dystonia, thigh adduction, thigh abduction knee flexion, knee extension, ankle flexion, ankle extension, equinovarus, deformity foot dystonia, striatal toe, toe flexion, toe extension, axial dystonia, pisa syndrome, belly dancer dystonia, segmental dystonia, hemidystonia, generalised dystonia, dystonia in lubag, dystonia in corticobasal degeneration, dystonia in lubag, tardive dystonia, dystonia in spinocerebellar ataxia, dystonia in Parkinson's disease, dystonia in Huntington's disease, dystonia in Hallervorden-Spatz disease, dopa-induced dyskinesias/dopa-induced dystonia, tardive dyskinesias/tardive dystonia, paroxysmal dyskinesias/dystonias, kinesiogenic non-kinesiogenic action-induced palatal myoclonus, myoclonus myokymia, rigidity, benign muscle cramps, hereditary chin trembling, paradoxic jaw muscle activity, hemimasticatory spasms, hypertrophic branchial myopathy, maseteric hypertrophy, tibialis anterior hypertrophy, nystagmus, oscillopsia supranuclear gaze palsy, epilepsia, partialis continua, planning of spasmodic torticollis operation, abductor vocal cord paralysis, recalcitrant mutational dysphonia, upper oesophageal sphincter dysfunction, vocal fold granuloma, stuttering Gilles de la Tourette syndrome, middle ear myoclonus, protective larynx closure, postlaryngectomy, speech failure, protective ptosis, entropion sphincter Odii dysfunction, pseudoachalasia, nonachalsia, oesophageal motor disorders, vaginismus, postoperative immobilisation tremor, bladder dysfunction, detrusor sphincter dyssynergia, bladder sphincter spasm, hemifacial spasm, reinnervation dyskinesias, cosmetic use craw's feet, frowning facial asymmetries, mentalis dimples, stiff person syndrome, tetanus prostate hyperplasia, adipositas, treatment infantile cerebral palsy strabismus, mixed paralytic concomitant, after retinal detachment surgery, after cataract surgery, in aphakia myositic strabismus, myopathic strabismus, dissociated vertical deviation, as an adjunct to strabismus surgery, esotropia, exotropia, achalasia, anal fissures, exocrine gland hyperactivity, Frey syndrome, Crocodile Tears syndrome, hyperhidrosis, axillar palmar plantar rhinorrhea, relative hypersalivation in stroke, in Parkinsosn's, in amyotrophic lateral sclerosis, spastic conditions, in encephalitis and myelitis autoimmune processes, multiple sclerosis, transverse myelitis, Devic syndrome, viral infections, bacterial infections, parasitic infections, fungal infections, in hereditary spastic paraparesis postapoplectic syndrome hemispheric infarction, brainstem infarction, myelon infarction, in central nervous system trauma, hemispheric lesions, brainstem lesions, myelon lesion, in central nervous system hemorrhage, intracerebral hemorrhage, subarachnoidal hemorrhage, subdural hemorrhage, intraspinal hemorrhage, in neoplasias, hemispheric tumors, brainstem tumors, or myelon tumor). Additional embodiments are described herein.

DESCRIPTION OF THE FIGURES

FIG. 3 shows the amino acid sequence of SEQ ID NO:1 (BoNT/FA).

DEFINITIONS

Figure 1:
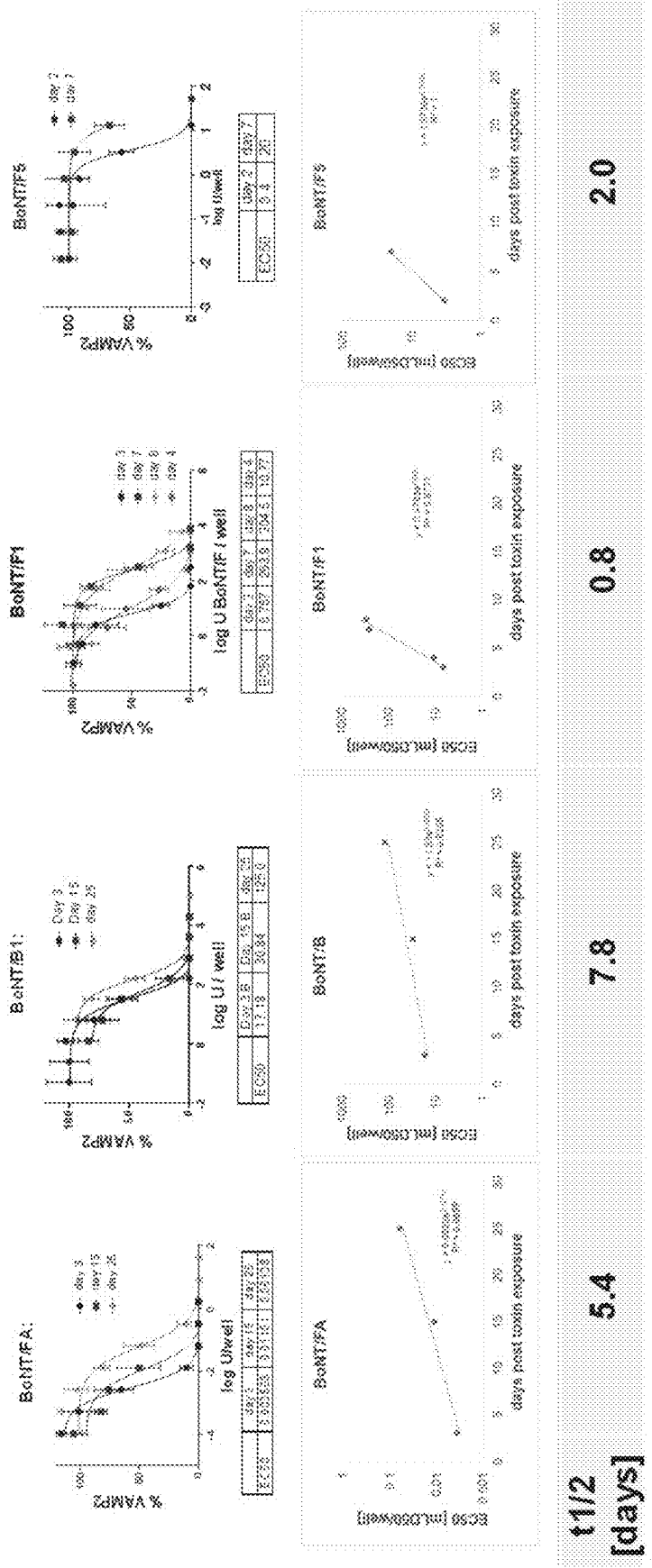
FIG. 1 shows potency of BoNT toxins in cultured human neurons.

To facilitate an understanding of the present disclosure, a number of terms and phrases are defined below:

As used herein, the term "exhibits one or more altered properties" (e.g., altered duration of action relative to wild type BoNT, altered neuronal selectivity relative to wild type BoNT, altered potency relative to wild type BoNT, altered onset of action relative to wild type BoNT, or altered uptake or transport relative to wild type BoNT) refers to a property of a variant or hybrid BoNT (e.g., those described herein) that is altered relative to a wild type BoNT.

As used herein, the term "host cell" refers to any eukaryotic or prokaryotic cell (e.g., bacterial cell, mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos and stem cell derived cells.

As used herein, the term "pharmaceutical composition" refers to the combination of an active agent with a carrier, inert or active, making the composition especially suitable for diagnostic or therapeutic use in vitro, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include cells, tissues, blood products, such as plasma, serum and the like. Such examples are not however to be construed as limiting the sample types applicable to the present disclosure.

DETAILED DESCRIPTION OF THE DISCLOSURE

The present disclosure relates to hybrid neurotoxins and uses thereof. In particular, provided herein are chimeric botulinum neurotoxins with altered properties and uses thereof (e.g., research, screening, and therapeutic uses).

Botulinum neurotoxins (BoNTs), produced by neurotoxigenic clostridial species, are the cause of the severe disease botulism in humans and animals. Early research on BoNTs has led to their classification into seven serotypes (serotypes A to G) based upon the selective neutralization of their toxicity in mice by homologous antibodies. Recently, a report of an eighth serotype of BoNT, designated "type H," has stirred controversy. This BoNT was produced together with BoNT/B2 in a dual-toxin-producing *Clostridium botulinum* strain. The data used to designate this novel toxin as a new serotype were derived from culture supernatant containing both BoNT/B2 and the novel toxin and from sequence information. However, data from two independent laboratories indicated neutralization by antibodies raised against BoNT/A1, and classification as BoNT/FA was proposed. The sequence data indicate a chimeric structure consisting of a BoNT/A1 receptor binding domain, a BoNT/F5 light-chain domain, and a novel translocation domain most closely related to BoNT/F1.

Described herein is characterization of this toxin (FIG. 3; SEQ ID NO:1) purified from the native strain in which expression of the second BoNT (BoNT/B) has been eliminated. Mass spectrometry analysis indicated that the toxin preparation contained only BoNT/FA and confirmed catalytic activity analogous to that of BoNT/F5. The in vivo mouse bioassay indicated a specific activity of this toxin of $3.8 \times 10^7$ mouse 50% lethal dose $(mLD_{50})/mg$, whereas activity in cultured human neurons was very high (50% effective concentration $[EC_{50}]$=0.02 mLD50/well). Neutralization assays in cells and mice both indicated full neutralization by various antibodies raised against BoNT/A1, although at 16- to 20-fold-lower efficiency than for BoNT/A1.

Figure 2:
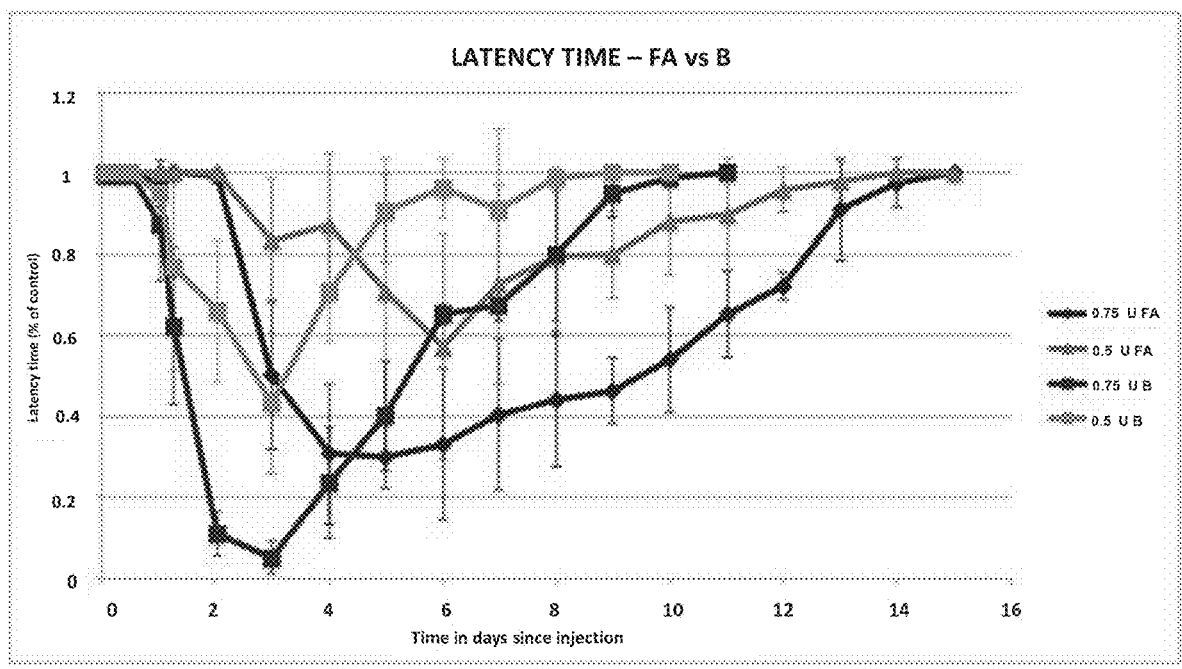
FIG. 2 shows a) duration of action of BoNT/FA, BoNT/F1, and BoNT/B1 in cultured hiPSC derived neurons; and b) and c) local and systemic effects in mice after intramuscular injection of BoNT/B1 or BoNT/FA.
Figure 2:
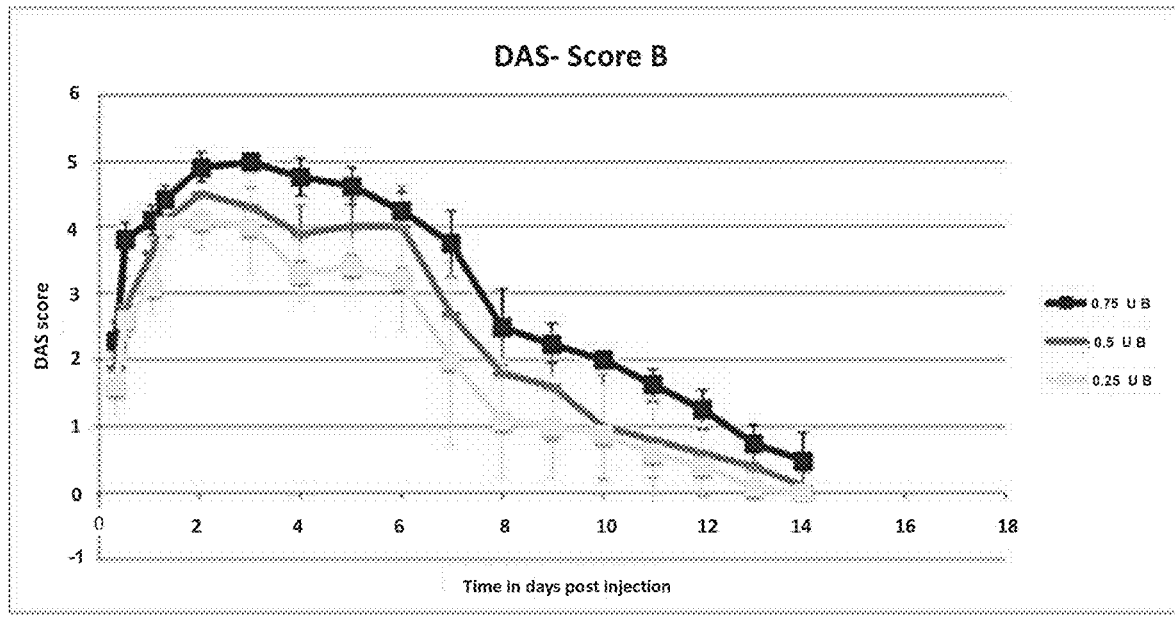

Further analyses of the purified BoNT/FA have revealed that, surprisingly, the half-life in cultured human neurons is similar to that of BoNT/B1 (currently marketed as Myobloc) (FIG. 1). This was unexpected because the light chain of this toxin is similar to BoNT/F, and BoNT/F serotypes are known to have a very short duration of action. In addition, local injection into mice resulted in a similar maximum local paralysis response and similar duration as BoNT/B1, however, systemic symptoms were milder at the same concentrations, had a later onset and slightly slower recovery (FIG. 2). This indicates that this toxin provides an alternative to BoNT/B1 as a local paralytic therapeutic and may have a larger safety margin. As with BoNT/B1, the therapeutic target is VAMP1 and 2, but this toxin enters cultured human neuronal cells about 10,000 fold more efficiently and has an at least similar duration of action as BoNT/B1. In addition, derivatives of BoNT/FA or engineered hybrid toxins maintaining specific structural domains of BoNT/FA yield therapeutics with advantageous and novel characteristics, such as faster cell entry and unique in vivo distribution.

This BoNT variant is over 10 fold more potent than BoNT/A1 and over 1000 fold more potent than BoNT/B1 in cultured human neurons (FIG. 1). While BoNT/A1 cleaves SNAP-25, BoNT/FA cleaves VAMP. BoNT/B1 also cleaves VAMP, but it does not enter human neurons as efficiently as BoNT/A1 and BoNT/FA. Importantly, BoNT/FA has similar duration of action in human neurons and in mice as BoNT/B1 and caused similar local paralysis but with milder overall motorneuron deficiency.

In some embodiments, BoNT molecules are prepared using a manufacturing process described, for example, in Dressler D. HNO. 2012 June; 60(6):496-502; Wortzman M S, Pickett A. Aesthet Surg J. 2009 November; 29(6 Suppl): S34-42; each of which is herein incorporated by reference in its entirety or another suitable method.

In some embodiments, BoNT molecules are provided as pharmaceutical compositions. The compounds described herein, optionally together with a conventional adjuvant, carrier, or diluent, may thus be placed into the form of pharmaceutical formulations of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

BoNT compositions are typically administered via injection, although other delivery methods are specifically contemplated.

The dose, when using the compounds and formulations described herein, can vary within wide limits and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds. Representative doses include, but not limited to, about 0.1 pg to about 5000 ng, about 0.001 ng to about 2500 ng, about 0.001 ng to about 1000 ng, 0.001 ng to about 500 ng, 0.001 ng to about 250 ng, about 0.001 ng to about 100 ng, about 0.001 ng to about 50 ng and about 0.001 ng to about 25 ng. Multiple doses may be administered during the day, especially when relatively large amounts are deemed to be needed, for example 2, 3 or 4 doses. Depending on the individual and as deemed appropriate from the patient's physician or caregiver it may be necessary to deviate upward or downward from the doses described herein.

The amount of active ingredient, for use in treatment will vary with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds described herein and as part of a drug combination. The dosage regimen for treating a disease condition with the compounds and/or compositions is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods described herein.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

For preparing pharmaceutical compositions, the selection of a suitable pharmaceutically acceptable carrier is typically liquid. Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed, as a solvent or suspending medium. For this purpose any bland fixed oil may be employed including synthetic mono- or diglycerides. In addition, fatty acids such as oleic acid find use in the preparation of injectables.

The compounds according may thus be formulated for parenteral administration (e.g. by injection, for example bolus injection or continuous infusion) and may be presented in unit dose form in ampoules, pre-filled syringes, small volume infusion or in multi-dose containers with an added preservative.

In some embodiments, compositions comprising BoNT molecules comprise purified BoNT stabilized and preserved, e.g. with human serum albumin and non-protein stabilizers. These may be derived from non-human and non-animal sources. In some embodiments, BoNTs are provided in combination with native complexes. In some embodiments, compositions are in a pH neutral buffer and stabilized with human serum albumin in stabilized liquid formulation. In some embodiments, compositions are lyophilized for resuspension in saline or sterile water.

The BoNT preparations described herein find use in the treatment of a variety of conditions including, but not limited to, cosmetic treatments and to temporarily relieve a variety of muscle spasticity disorders, hyperhydrosis and migraines (Chaddock J A & Acharya K R (2011) *FEBS J* 278: 899-904; Dressler, D. Clinical applications of botulinum toxin. In Curr opin microbiol, England, 2012; Vol. 15, pp 325-336; Dressler, D. Botulinum toxin drugs: Brief history and outlook. J Neural Transm (Vienna) 2016, 123, 277-279). Cosmetic and clinical applications of BoNTs are increasing, and new formulations of BoNTs for pharmaceutical purposes are being developed necessitating clinical trials, accurate potency determination, and neutralizing antibody screening. For example, BoNTs are pharmaceutically administered for the treatment of pain disorders, voluntary muscle strength, focal dystonia, including cervical, cranial dystonia, and benign essential blepharospasm, hemifacial spasm, and focal spasticity, gastrointestinal disorders, hyperhidrosis, and cosmetic wrinkle correction, Blepharospasm, oromandibular dystonia, jaw opening type, jaw closing type, bruxism, Meige syndrome, lingual dystonia, apraxia of eyelid, opening cervical dystonia, antecollis, retrocollis, laterocollis, torticollis, pharyngeal dystonia, laryngeal dystonia, spasmodic dysphonia/adductor type, spasmodic dysphonia/abductor type, spasmodic dyspnea, limb dystonia, arm dystonia, task specific dystonia, writer's cramp, musician's cramps, golfer's cramp, leg dystonia, thigh adduction, thigh abduction knee flexion, knee extension, ankle flexion, ankle extension, equinovarus, deformity foot dystonia, striatal toe, toe flexion, toe extension, axial dystonia, pisa syndrome, belly dancer dystonia, segmental dystonia, hemidystonia, generalised dystonia, dystonia in lubag, dystonia in corticobasal degeneration, dystonia in lubag, tardive dystonia, dystonia in spinocerebellar ataxia, dystonia in Parkinson's disease, dystonia in Huntington's disease, dystonia in Hallervorden-Spatz disease, dopa-induced dyskinesias/dopa-induced dystonia, tardive dyskinesias/tardive dystonia, paroxysmal dyskinesias/dystonias, kinesiogenic non-kinesiogenic action-induced palatal myoclonus, myoclonus myokymia, rigidity, benign muscle cramps, hereditary chin trembling, paradoxic jaw muscle activity, hemimasticatory spasms, hypertrophic branchial myopathy, maseteric hypertrophy, tibialis anterior hypertrophy, nystagmus, oscillopsia supranuclear gaze palsy, epilepsia, partialis continua, planning of spasmodic torticollis operation, abductor vocal cord paralysis, recalcitant mutational dysphonia, upper oesophageal sphincter dysfunction, vocal fold granuloma, stuttering Gilles de la Tourette syndrome, middle ear myoclonus, protective larynx closure, postlaryngectomy, speech failure, protective ptosis, entropion sphincter Odii dysfunction, pseudoachalasia, nonachalsia, oesophageal motor disorders, vaginismus, postoperative immobilisation tremor, bladder dysfunction, detrusor sphincter dyssynergia, bladder sphincter spasm, hemifacial spasm, reinnervation dyskinesias, cosmetic use craw's feet, frowning facial asymmetries, mentalis dimples, stiff person syndrome, tetanus prostate hyperplasia, adipositas, treatment infantile cerebral palsy strabismus, mixed paralytic concomitant, after retinal detachment surgery, after cataract surgery, in aphakia myositic strabismus, myopathic strabismus, dissociated vertical deviation, as an adjunct to strabismus surgery, esotropia, exotropia, achalasia, anal fissures, exocrine gland hyperactivity, Frey syndrome, Crocodile Tears syndrome, hyperhidrosis, axillar palmar plantar rhinorrhea, relative hypersalivation in stroke, in Parkinsosn's, in amyotrophic lateral sclerosis, spastic conditions, in encephalitis and myelitis autoimmune processes, multiple sclerosis, transverse myelitis, Devic syndrome, viral infections, bacterial infections, parasitic infections, fungal infections, in hereditary spastic paraparesis postapoplectic syndrome hemispheric infarction, brainstem infarction, myelon infarction, in central nervous system trauma, hemispheric lesions, brainstem lesions, myelon lesion, in central nervous system hemorrhage, intracerebral hemorrhage, subarachnoidal hemorrhage, subdural hemorrhage, intraspinal hemorrhage, in neoplasias, hemispheric tumors, brainstem tumors, and myelon tumor.

EXPERIMENTAL

Example 1

This Example describes properties of BoNT/B1, BoNT/F1, and BoNT/FA.

HiPSC derived neurons were exposed to serial dilutions of BoNT/B1, BoNT/F1, or BoNT/FA for 48 h followed by removal of all extracellular toxin. Cells were incubated at 37° C., fed every 2-3 days, and harvested at the indicated time points after toxin exposure. The percentage of VAMP2 cleavage was determined by Western blot and densitometry. The EC50 values were determined by curve fit using PRISM6 software, and the half-life ($t\frac{1}{2}$) for LC activity, as measured by VAMP2 recovery, was calculated from derived EC50 values at the three time points. Results are shown in FIG. 1.

The indicated doses of BoNT/FA or BoNT/B1 were injected into the gastrocnemius muscle of ICR mice. The onset and duration of local paralysis were determined by DAS assay using a scale from 0 (no symptoms) to 5 (maximal paralysis), and overall (systemic) motorneuron deficiency was measured by Rotarod using an accelerating cycle (4-40 rpm over 5 min) and measuring the amount of time mice remained running on the rod (latency time). Results are shown in FIG. 2.

All publications, patents, patent applications and accession numbers mentioned in the above specification are herein incorporated by reference in their entirety. Although the disclosure has been described in connection with specific embodiments, it should be understood that the disclosure as claimed should not be unduly limited to such specific embodiments. Indeed, various modifications and variations of the described compositions and methods of the disclosure will be apparent to those of ordinary skill in the art and are intended to be within the scope of the following claims.

---

We claim:

1. A composition comprising a BoNT/FA toxin having an amino acid sequence selected from the group consisting of SEQ ID NO:1 and sequences at least 90% identical to SEQ ID NO:1.

2. The composition of claim 1, wherein said BoNT/FA has an amino acid sequence at least 95% identical to SEQ ID NO:1.

3. The composition of claim 1, wherein said BoNT/FA has an amino acid sequence at least 98% identical to SEQ ID NO:1.

4. The composition of claim 1, wherein said BoNT/FA has the amino acid sequence of SEQ ID NO:1.

5. A composition comprising a chimeric BoNT, comprising: a heavy chain BoNT/FA sequence comprising at least a portion of SEQ ID NO:1 and a light chain sequence from a different serotype of BoNT or a light chain BoNT/FA sequence comprising at least a portion of SEQ ID NO:1 and a heavy chain sequence from a different serotype of BoNT.

6. The composition of claim 1, wherein said composition is a pharmaceutical composition.

7. The composition of claim 6, wherein said composition further comprises a pharmaceutically acceptable carrier.

* * * * *

SEQUENCE LISTING

```
<160> NUMBER OF SEQ ID NOS: 1

<210> SEQ ID NO 1
<211> LENGTH: 1288
<212> TYPE: PRT
<213> ORGANISM: Artificial sequence
<220> FEATURE:
<223> OTHER INFORMATION: Synthetic peptide

<400> SEQUENCE: 1

Met Pro Val Val Ile Asn Ser Phe Asn Tyr Asp Asp Pro Val Asn Asp
1               5                   10                  15

Asn Thr Ile Ile Tyr Ile Arg Pro Pro Tyr Tyr Glu Thr Ser Asn Thr
                20                  25                  30

Tyr Phe Lys Ala Phe Gln Ile Met Asp Asn Val Trp Ile Ile Pro Glu
            35                  40                  45

Arg Tyr Arg Leu Gly Ile Asp Pro Ser Leu Phe Asn Pro Pro Val Ser
        50                  55                  60

Leu Lys Ala Gly Ser Asp Gly Tyr Phe Asp Pro Asn Tyr Leu Ser Thr
65                  70                  75                  80

Asn Thr Glu Lys Asn Lys Tyr Leu Gln Ile Met Ile Lys Leu Phe Lys
                85                  90                  95

Arg Ile Asn Ser Lys Pro Ala Gly Gln Ile Leu Leu Glu Glu Ile Lys
            100                 105                 110

Asn Ala Ile Pro Tyr Leu Gly Asn Ser Tyr Thr Gln Glu Glu Gln Phe
        115                 120                 125

Thr Thr Asn Asn Arg Thr Val Ser Phe Asn Val Lys Leu Ala Asn Gly
    130                 135                 140

Asn Ile Val Gln Gln Met Ala Asn Leu Ile Ile Trp Gly Pro Gly Pro
145                 150                 155                 160
```

```
Asp Leu Thr Thr Asn Lys Thr Gly Gly Ile Ile Tyr Ser Pro Tyr Gln
            165                 170                 175

Ser Met Glu Ala Thr Pro Tyr Lys Asp Gly Phe Gly Ser Ile Met Thr
            180                 185                 190

Val Glu Phe Ser Pro Glu Tyr Ala Thr Ala Phe Asn Asp Ile Ser Ile
            195                 200                 205

Ala Ser His Ser Pro Ser Leu Phe Ile Lys Asp Pro Ala Leu Ile Leu
            210                 215                 220

Met His Glu Leu Ile His Val Leu His Gly Leu Tyr Gly Thr Tyr Ile
225                 230                 235                 240

Thr Glu Tyr Lys Ile Thr Pro Asn Val Val Gln Ser Tyr Met Lys Val
            245                 250                 255

Thr Lys Pro Ile Thr Ser Ala Glu Phe Leu Thr Phe Gly Gly Arg Asp
            260                 265                 270

Arg Asn Ile Val Pro Gln Ser Ile Gln Ser Gln Leu Tyr Asn Lys Val
            275                 280                 285

Leu Ser Asp Tyr Lys Arg Ile Ala Ser Arg Leu Asn Lys Val Asn Thr
            290                 295                 300

Ala Thr Ala Leu Ile Asn Ile Asp Glu Phe Lys Asn Leu Tyr Glu Trp
305                 310                 315                 320

Lys Tyr Gln Phe Ala Lys Asp Ser Asn Gly Val Tyr Ser Val Asp Leu
            325                 330                 335

Asn Lys Phe Glu Gln Leu Tyr Lys Lys Ile Tyr Ser Phe Thr Glu Phe
            340                 345                 350

Asn Leu Ala Tyr Glu Phe Lys Ile Lys Thr Arg Leu Gly Tyr Leu Ala
            355                 360                 365

Glu Asn Phe Gly Pro Phe Tyr Leu Pro Asn Leu Leu Asp Asp Ser Ile
            370                 375                 380

Tyr Thr Glu Val Asp Gly Phe Asn Ile Gly Ala Leu Ser Ile Asn Tyr
385                 390                 395                 400

Gln Gly Gln Asn Ile Gly Ser Asp Ile Asn Ser Ile Lys Lys Leu Gln
            405                 410                 415

Gly Gln Gly Val Val Ser Arg Val Val Arg Leu Cys Ser Asn Ser Asn
            420                 425                 430

Thr Lys Asn Ser Leu Cys Ile Thr Val Asn Asn Arg Asp Leu Phe Phe
            435                 440                 445

Ile Ala Ser Gln Glu Ser Tyr Gly Glu Asn Thr Ile Asn Thr Tyr Lys
            450                 455                 460

Glu Ile Asp Asp Thr Thr Thr Leu Asp Pro Ser Phe Glu Asp Ile Leu
465                 470                 475                 480

Asp Lys Val Ile Leu Asn Phe Asn Glu Gln Val Ile Pro Gln Met Pro
            485                 490                 495

Asn Arg Asn Val Ser Thr Asp Ile Gln Lys Asp Asn Tyr Ile Pro Lys
            500                 505                 510

Tyr Asp Tyr Asn Arg Thr Asp Ile Ile Asp Ser Tyr Glu Val Gly Arg
            515                 520                 525

Asn Tyr Asn Thr Phe Phe Tyr Leu Asn Ala Gln Lys Phe Ser Pro Asn
            530                 535                 540

Glu Ser Asn Ile Thr Leu Thr Ser Ser Phe Asp Thr Gly Leu Leu Glu
545                 550                 555                 560

Gly Ser Lys Val Tyr Thr Phe Phe Ser Ser Asp Phe Ile Asn Asn Ile
            565                 570                 575
```

-continued

Asn Lys Pro Val Gln Ala Leu Leu Phe Ile Glu Trp Val Lys Gln Val
            580                 585                 590
Ile Arg Asp Phe Thr Thr Glu Ala Thr Lys Thr Ser Thr Val Asp Lys
        595                 600                 605
Leu Lys Asp Ile Ser Leu Val Val Pro Tyr Ile Gly Leu Ala Leu Asn
    610                 615                 620
Ile Gly Asp Glu Ile Tyr Lys Gln His Phe Ala Glu Ala Val Glu Leu
625                 630                 635                 640
Val Gly Ala Gly Leu Leu Leu Glu Phe Ser Pro Glu Phe Leu Ile Pro
                645                 650                 655
Thr Leu Leu Ile Phe Thr Ile Lys Gly Tyr Leu Thr Gly Ser Ile Arg
            660                 665                 670
Asp Lys Asp Lys Ile Ile Lys Thr Leu Asp Asn Ala Leu Asn Val Arg
        675                 680                 685
Asp Gln Lys Trp Lys Glu Leu Tyr Arg Trp Val Val Ser Lys Trp Leu
    690                 695                 700
Thr Thr Ile Asn Thr Gln Phe Asn Lys Arg Lys Glu Gln Met Tyr Lys
705                 710                 715                 720
Ala Leu Lys Asn Gln Ala Thr Ala Ile Lys Lys Ile Glu Asn Lys
                725                 730                 735
Tyr Asn Asn Tyr Thr Thr Asp Glu Lys Ser Lys Ile Asp Ser Ser Tyr
            740                 745                 750
Asn Ile Asn Glu Ile Glu Arg Thr Leu Asn Glu Lys Ile Asn Leu Ala
        755                 760                 765
Met Lys Asn Ile Glu Gln Phe Ile Thr Glu Ser Ser Ile Ala Tyr Leu
    770                 775                 780
Ile Asn Ile Ile Asn Asn Glu Thr Ile Gln Lys Leu Lys Ser Tyr Asp
785                 790                 795                 800
Asp Leu Val Arg Arg Tyr Leu Leu Gly Tyr Ile Arg Asn His Ser Ser
                805                 810                 815
Ile Leu Gly Asn Ser Val Glu Glu Leu Asn Ser Lys Val Asn Asn His
            820                 825                 830
Leu Asp Asn Gly Ile Pro Phe Glu Leu Ser Ser Tyr Thr Asn Asp Ser
        835                 840                 845
Leu Leu Ile Arg Tyr Phe Asn Lys Asn Tyr Gly Glu Leu Lys Tyr Asn
    850                 855                 860
Cys Ile Leu Asn Ile Lys Tyr Glu Met Asp Arg Asp Lys Leu Val Asp
865                 870                 875                 880
Ser Ser Gly Tyr Arg Ser Arg Ile Asn Ile Gly Thr Gly Val Lys Phe
                885                 890                 895
Ser Glu Ile Asp Lys Asn Gln Val Gln Leu Ser Asn Leu Glu Ser Ser
            900                 905                 910
Lys Ile Glu Val Ile Leu Asn Asn Gly Val Ile Tyr Asn Ser Met Tyr
        915                 920                 925
Glu Asn Phe Ser Thr Ser Phe Trp Ile Arg Ile Pro Lys Tyr Phe Arg
    930                 935                 940
Asn Ile Asn Asn Glu Tyr Lys Ile Ile Ser Cys Met Gln Asn Asn Ser
945                 950                 955                 960
Gly Trp Glu Val Ser Leu Asn Phe Ser Asn Met Asn Ser Lys Ile Ile
                965                 970                 975
Trp Thr Leu Gln Asp Thr Glu Gly Ile Lys Lys Thr Val Val Phe Gln
            980                 985                 990
Tyr Thr Gln Asn Ile Asn Ile Ser  Asp Tyr Ile Asn Arg Trp Ile Phe

```
                995                 1000                1005
Val Thr Ile Thr Asn Asn Arg Leu Ser Asn Ser Lys Ile Tyr Ile
    1010                1015                1020

Asn Gly Arg Leu Ile Asn Glu Glu Ser Ile Ser Asp Leu Gly Asn
    1025                1030                1035

Ile His Ala Ser Asn Asn Ile Met Phe Lys Leu Asp Gly Cys Arg
    1040                1045                1050

Asp Pro His Arg Tyr Ile Trp Ile Lys Tyr Phe Asn Leu Phe Asp
    1055                1060                1065

Lys Glu Leu Asn Lys Lys Glu Ile Lys Asp Leu Tyr Asp Asn Gln
    1070                1075                1080

Ser Asn Ser Gly Ile Leu Lys Asp Phe Trp Gly Asp Tyr Leu Gln
    1085                1090                1095

Tyr Asp Lys Pro Tyr Tyr Met Leu Asn Leu Tyr Asp Pro Asn Lys
    1100                1105                1110

Tyr Leu Asp Val Asn Asn Val Gly Ile Arg Gly Tyr Met Tyr Leu
    1115                1120                1125

Lys Gly Pro Arg Gly Arg Ile Val Thr Thr Asn Ile Tyr Leu Asn
    1130                1135                1140

Ser Thr Leu Tyr Met Gly Thr Lys Phe Ile Ile Lys Lys Tyr Ala
    1145                1150                1155

Ser Gly Asn Lys Asp Asn Ile Val Arg Asn Asn Asp Arg Val Tyr
    1160                1165                1170

Ile Asn Val Val Val Lys Asn Lys Glu Tyr Arg Leu Ala Thr Asn
    1175                1180                1185

Ala Ser Gln Ala Gly Val Glu Lys Ile Leu Ser Ala Val Glu Ile
    1190                1195                1200

Pro Asp Val Gly Asn Leu Ser Gln Val Val Val Met Lys Ser Glu
    1205                1210                1215

Asn Asp Gln Gly Ile Arg Asn Lys Cys Lys Met Asn Leu Gln Asp
    1220                1225                1230

Asn Asn Gly Asn Asp Ile Gly Phe Ile Gly Phe His Gln Phe Asn
    1235                1240                1245

Asn Ile Ala Lys Leu Val Ala Ser Asn Trp Tyr Asn Arg Gln Ile
    1250                1255                1260

Gly Lys Ala Ser Arg Thr Phe Gly Cys Ser Trp Glu Phe Ile Pro
    1265                1270                1275

Val Asp Asp Gly Trp Gly Glu Ser Ser Leu
    1280                1285
```